US009416373B2

(12) United States Patent
Franco Puntes et al.

(10) Patent No.: US 9,416,373 B2
(45) Date of Patent: Aug. 16, 2016

(54) BIOGAS PRODUCTION

(75) Inventors: Víctor Franco Puntes, Barcelona (ES); Edgar Emir González, Sant Cugat del Vallès (ES); Eudald Casals Mercadal, Cerdanyola del Vallès (ES); Ana Garcia Mestre, Molins de Rei (ES); Lucia Delgado Ramisa, Barcelona (ES); Xavier Font Segura, Arenys de Mar (ES); Antonio Sánchez Ferrer, Barecelona (ES)

(73) Assignees: FUNDACIÓ PRIVADA INSTITUT CATALÁ DE NANOTECHOLOGIA, Bellatera (Barcelona) (ES); INSTITUCIÓ CATALANA DE RECERCA I ESTUDIS AVANÇATS, Barcelona (ES); UNIVERSITAT AUTÒNOMA DE BARCELONA, Bellatera (Barcelona) (ES)

( * ) Notice: Subject to any disclaimer, the term of this patent is extended or adjusted under 35 U.S.C. 154(b) by 338 days.

(21) Appl. No.: 14/004,646

(22) PCT Filed: Mar. 8, 2012

(86) PCT No.: PCT/EP2012/054022
§ 371 (c)(1),
(2), (4) Date: Oct. 4, 2013

(87) PCT Pub. No.: WO2012/123331
PCT Pub. Date: Sep. 20, 2012

(65) Prior Publication Data
US 2014/0017753 A1    Jan. 16, 2014

(30) Foreign Application Priority Data

Mar. 11, 2011    (EP) ..................... 11157784

(51) Int. Cl.
| | |
|---|---|
| *C12P 5/02* | (2006.01) |
| *C02F 3/00* | (2006.01) |
| *C02F 3/08* | (2006.01) |
| *C02F 1/68* | (2006.01) |
| *C02F 3/28* | (2006.01) |
| *C02F 11/04* | (2006.01) |
| *C02F 1/48* | (2006.01) |

(52) U.S. Cl.
CPC . *C12P 5/023* (2013.01); *C02F 1/68* (2013.01); *C02F 3/08* (2013.01); *C02F 3/28* (2013.01); *C02F 11/04* (2013.01); *C02F 1/48* (2013.01); *Y02E 50/343* (2013.01)

(58) Field of Classification Search
None
See application file for complete search history.

(56) References Cited

U.S. PATENT DOCUMENTS

| 4,735,725 A | 4/1988 | Reischl et al. |
| 4,981,593 A | 1/1991 | Priestley et al. |

FOREIGN PATENT DOCUMENTS

| EP | 2159198 A1 | 3/2010 |
| KR | 20040087814 A | 10/2004 |
| WO | WO2008141631 A1 | 11/2008 |

OTHER PUBLICATIONS

Barrena, Raquel et al, "Evaluation of the ecotoxicity of model nanoparticles", Chemosphere vol. 75, issue 7, pp. 850-857, May 2009, Elsevier Ltd. New York, NY.
Brar, Satinder K. et al. : "Engineered nanoparticles in wastewater and wastewater sludge Evidence and impacts", Waste Management, vol. 30, issue 3, Mar. 2010, Elsevier Ltd. New York, NY.
Massart Rene, "Preparation of Aqueous Magnetic Liquids in Alkaline and Acidic Media", IEEE Transactions on Magnetics vol. 17. No. 2, pp. 1247-1248, Mar. 1981, IEEE Magnetics Society Carpentersville, IL.
I. Nyiro-Kosa, D. Csakberenyi Nagy and M. Posfai. Size and shape control of precipitated magnetite nanoparticles. European Journal of Mineralogy, 2009, vol. 21, pp. 293-302 Schweizerbart science publishers, Stuttgart, Germany.
M. Posfai et al: "Iron Oxides and Sulfides in Magnetotactic Bacteria: Electron Holography of Magnetic Microstructureand Electron Tomography of Crystal Morphology", Jul. 17, 2005, pp. 1-4, XP002649748, Retrieved from the Internet: URL:http://homepage.mac.com/tkasama/takeshi/PDF files/Posfai_MCM05.pdf [retrieved on Jul. 12, 2011].
International Search Report and Written Opinion of the International Searching Authority. International Application No. PCT/EP2012/054022, issued by the European Patent Office, mail date May 18, 2012, 8 pages, Rijswijk Netherlands.
DIN 38414, German Ordinance—Ordinance on Environmentally Compatible Storage of Waste from Human Settlements and on Biological Waste-Treatment Facilities, Articles 1-4, Feb. 20, 2001, 50 pages, The Federal Chancellor Gerhard Schröder the Federal Minister for the Environment, Nature Conservation and Nuclear Safety Jürgen Trittin, Berlin Germany.

*Primary Examiner* — Jennifer McDonald
*Assistant Examiner* — Qing Xu
(74) *Attorney, Agent, or Firm* — Peter B. Scull; Hamilton, DeSanctis and Cha, LLP

(57) ABSTRACT

A process for the production of biogas from biodegradable material is disclosed, the process comprising the steps of: (a) adding the biodegradable material to the reactor; (b) inoculating a microorganism; (c) adding a colloidal solution of surface-modified iron oxide nanoparticles to the reactor; (d) providing anaerobic conditions; (e) carrying out an anaerobic digestion; and (f) collecting the biogas; wherein the steps (a), (b) and (c) can be carried out in any order.

18 Claims, 4 Drawing Sheets

BIOGAS PRODUCTION

The present invention relates to a process for the production of biogas, as well as to the use of metallic nanoparticles in the biogas production.

BACKGROUND ART

Biogas is a sustainable alternative source of energy, for example can be used as a low cost fuel, but to date there is still a lack of efficiency in its production.

Biogas is produced from the anaerobic digestion of organic matter such as animal manure, sewage, and municipal solid waste. The process produces methane and carbon dioxide. After the biogas is processed to required standards of purity, biogas becomes a renewable substitute for natural gas and can be used to fuel natural gas vehicles, helping to replace fossil fuels.

Anaerobic digestion is a series of processes in which microorganisms break down biodegradable material in the absence of oxygen, used for industrial or domestic purposes to manage waste and/or to release energy. It is widely used as part of the process to treat wastewater. As part of an integrated waste management system, anaerobic digestion reduces the emission of landfill gas into the atmosphere. Anaerobic digestion is widely used as a renewable energy source because the process produces a methane and carbon dioxide rich biogas suitable for energy production, helping to replace fossil fuels. The nutrient-rich digested biomass which is also produced can be used as fertiliser. The technical expertise required to maintain industrial scale anaerobic digesters coupled with high capital costs and low process efficiencies had limited the level of its industrial application as a waste treatment technology.

Many attempts have been performed in order to increase biogas production, including thermal or ultrasound pre-treatment of organic waste, but all of them present limited industrial applications.

Additionally, iron has been shown to enhance anaerobic digestion, but there are severe drawbacks for introducing the metal ion in an anaerobic closed reactor. For example, the addition of large iron oxide macroscopic crystal lacks concentration control, thus, either the ions iron concentration is too high at the beginning or it reaches too low concentration too rapidly.

US patent application U.S. Pat. No. 4,981,593 describes a process for removing of suspended impurities from residual waters. This document describes that carrying out an anaerobic digestion with magnetite particles of size about 50-100 mm allows removing the $H_2S$ from the reactor environment. It also describes the strong tendency for sewage organics to co-flocculate with coagulant/adsorbents such as magnetite, a ferromagnetic mineral with chemical formula $Fe_3O_4$ and that coagulant/adsorbent particles should have a particle size of 2 $10^{-5}$ m or less, preferably $10^{-6}$ to $10^{-5}$ m. However, the results of digester operation with the organic material still attached to the magnetite particles of size about to $10^{-6}$-$10^{-5}$ m, were disappointing. The gas production was an order of magnitude below what would be expected from a digester. As a result, the document concludes that improved digestion can be achieved by stripping and separating the concentrated sewage material from the magnetite particles and then feeding the resultant slurry to an anaerobic digester. In this document it is also described that the anaerobic digester may contain magnetite particles of size about 50-100 mm. This means that this patent publication describes that when the particle size of magnetite increase the gas production increase too.

Thus, from what is known in the art, it is derived that the development of a process for the production of biogas is still of great interest.

SUMMARY OF THE INVENTION

Inventors have found that the use of iron oxide nanoparticles in the process for the production of biogas, from biodegradable material via an anaerobic digestion results in an increase of biogas production. The process is advantageous since an increase in the efficiency results in a more cost-efficient process. This fact is considered an important contribution to the art since precisely, the use of industrial scale anaerobic digesters known in the art as a waste treatment technology had limited use mainly due to high capital costs and low process efficiencies.

Nothing in the art suggests that the use of iron oxide nanoparticles in anaerobic digestions could increase the biogas production, in fact, the patent U.S. Pat. No. 4,981,593 teaches away from the invention, since it discloses that when the size of magnetite particles is reduced from millimeters to microns the gas production decreases in an order of magnitude from what would be expected.

Therefore, an aspect of the present invention relates to a process for the production of biogas from biodegradable material which comprises the following steps: (a) adding the biodegradable material to the digester; (b) inoculating the microorganisms; (c) adding a colloidal solution of the surface-modified iron oxide nanoparticles to the digester; (d) providing anaerobic conditions; (e) carrying on the anaerobic reaction; (f) collecting the biogas; wherein the steps (a), (b) and (c) can be carried out in any order. The anaerobic reaction (step (e)) thus proceeds in the presence of the surface-modified iron oxide nanoparticles.

The nanoparticles of iron oxide dissolve in the media which is advantageous because it allows the presence of iron cations in the media. In addition, nanoparticles ensure a homogeneous distribution of the iron ions in the solution; the nanoparticles can be used to maintain a sustained supply of iron ions to the reactor. The concentration of the nanoparticles is sustained at a determined concentration for a longer time avoiding the high concentrations corresponding to the inoculation and avoiding the rapid decrease of the concentration.

Therefore, another aspect of the present invention relates to a used of iron oxide nanoparticles for biogas production in anaerobic conditions.

DETAILED DESCRIPTION OF THE INVENTION

Figure 1:
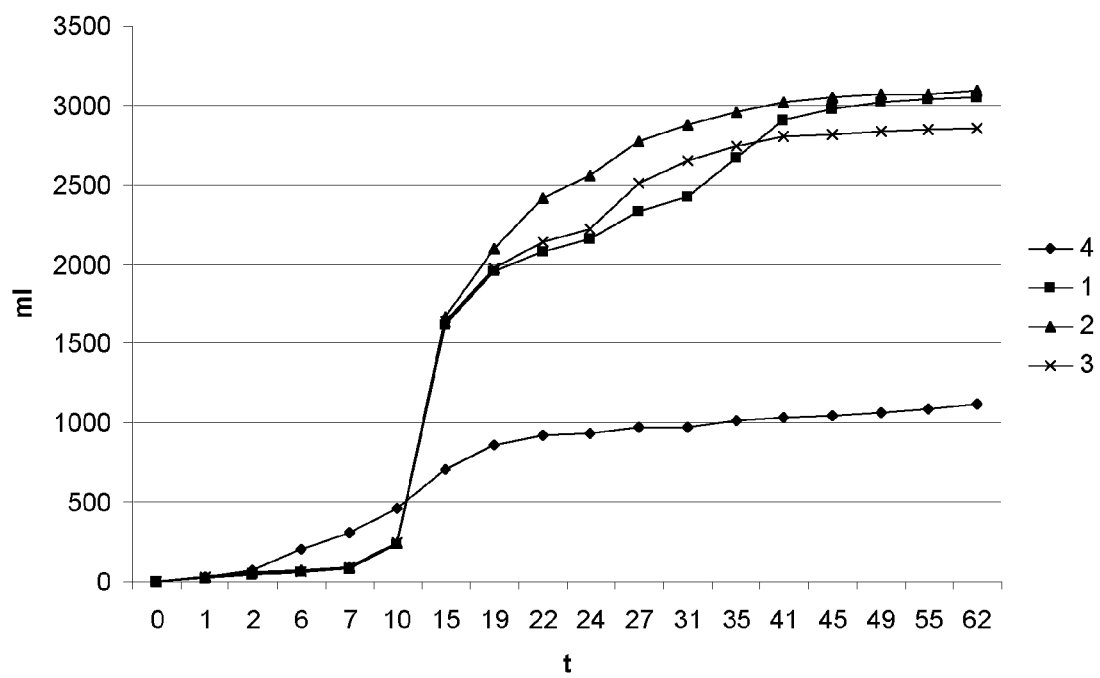
FIG. 1 shows a plot of the production of biogas (ml) versus time, t (days), in the presence of $Fe_3O_4$ nanoparticles (three replicates, (1), (2), (3)). The control (4) without nanoparticles, is also presented in FIG. 1.

The term "biogas" as used herein, refers to a gas produced by the biological breakdown of organic material in the absence of oxygen. Biogas is produced by anaerobic digestion of biodegradable materials. This type of biogas comprises primarily methane and carbon dioxide.

The term "biodegradable material" as used herein, refers to organic material capable of being converted usually by bacteria and other microorganisms into basic elements as methane and $CO_2$.

The term "colloidal solution" as used herein, refers to a dispersion of two phases, a dispersed phase, the $Fe_3O_4$ nanoparticles, and a dispersion medium, the solvent.

The term "surface-modified" as used herein, refers to a post synthesis treatment to modify the iron based nanoparticle or the surface modified can be formed directly in the presence of a surface coating material. Examples of surface coating materials are functional materials such hydroxy compounds, metal oxide, phosphates, sulphates, carboxylates, polymers, or serum proteins.

The term "nanoparticle" as used herein, refers a particle with all three dimensions at the nanoscale, where the nanoscale is the range about 3 nm to about 100 nm.

The term "anaerobic conditions" as used herein, refers to the absence of oxygen.

The term "anaerobic digestion" as used herein, refers to a series of processes in which microorganisms break down biodegradable material in the absence of oxygen used for industrial or domestic purposes to manage waste and/or to release energy.

As mentioned above, an aspect of the present invention relates to a process for the production of biogas from biodegradable material which comprises the following steps: (a) adding the biodegradable material to the digester; (b) inoculating the microorganisms; (c) adding a colloidal solution of the surface-modified iron oxide nanoparticles to the digester; (d) providing anaerobic conditions; (e) carrying on the anaerobic reaction; (f) collecting the biogas; wherein the steps (a), (b) and (c) can be carried out in any order. The anaerobic reaction thus proceeds in the presence of the surface-modified iron oxide nanoparticles.

The colloidal solution of surface modified iron oxide nanoparticles is stable avoiding the aggregation of nanoparticles. This colloidal solution is not toxic because the amount of $Fe_3O_4$ added is lower than in the case of addition of macro particles of $Fe_3O_4$. The amount of $Fe_3O_4$ can be small because by introducing iron oxide in the form of nanoparticles, it is possible supply the iron ions steadily, favouring a sustained biogas production which ends when the organic material is depleted.

In a particularly embodiment, the invention provides a process for the production of biogas from biodegradable material consisting of the steps (a) to (f) as mentioned above, wherein the steps (a), (b) and (c) can be carried out in any order and step (e) is carried out consecutively to steps (a), (b) and (c).

In another particular embodiment, the invention provides a process for the production of biogas from biodegradable material consisting of the steps (a) to (f) as mentioned above, wherein the steps (a), (b) and (c) can be carried out in any order.

In another particular embodiment, the iron oxide nanoparticles are $Fe_3O_4$ nanoparticles. In another particular embodiment the surfaces of the iron oxide nanoparticles are hydroxylated or coated with serum proteins.

In a preferred embodiment the diameter of the iron oxide nanoparticles are between 3 nm and 100 nm. In another preferred embodiment the diameter of the iron oxide nanoparticles is between 5 nm and 90 nm. In another preferred embodiment the diameter of the iron oxide nanoparticles is between 5 nm and 50 nm. In a more preferred embodiment the diameter of the iron oxide nanoparticles is between 7 nm and 20 nm.

In other preferred embodiments the concentration of the iron oxide nanoparticles in the solvent is between 0.5 and 1 mg/ml. In other preferred embodiments the concentration of the iron oxide nanoparticles in the solvent is between 0.6 and 0.9 mg/ml. In a more preferred embodiment the concentration of the iron oxide nanoparticles in the solvent is between 0.7 and 0.8 mg/ml.

Examples of solvents are deoxygenated tetramethylammonium hydroxide, inorganic salts, for example sodium hydroxide and sodium citrate and serun serum proteins.

In another preferred embodiment the reaction temperature is between 30° C. and 70° C. In a more preferred embodiment the reaction temperature is between 40° C. and 60° C.

In another preferred embodiment the biodegradable material is sludge from waste water treatment plant, industrial residues, urban solid residues, animal by-products or agricultural waste.

In another preferred embodiment the microorganisms are acidogenic bacteria, acetogenic bacteria and/or methanogen archea. In a particular embodiment the microorganisms are mesophilic bacteria.

As mentioned above another aspect of the present invention relates to the use of iron oxide nanoparticles according to the invention for biogas production in anaerobic conditions. Preferably, the iron oxide nanoparticles used for these purposes are the iron oxide nanoparticles defined in the particular and preferred embodiments mentioned above.

Thus, in a particular embodiment of this aspect, the iron oxide nanoparticles are $Fe_3O_4$ nanoparticles. In another particular embodiment of this aspect, the surfaces of the iron oxide nanoparticles are hydroxylated or coated with serum proteins.

In a preferred embodiment of this aspect, the diameter of the iron oxide nanoparticles is between 3 nm and 100 nm. In another preferred embodiment the diameter of the iron oxide nanoparticles is between 5 nm and 90 nm. In another preferred embodiment the diameter of the iron oxide nanoparticles is between 5 nm and 50 nm. In another preferred embodiment the diameter of the iron oxide nanoparticles is between 5 nm and 30 nm. In a more preferred embodiment the diameter of the iron oxide nanoparticles is between 7 nm and 20 nm.

In another preferred embodiment of this aspect the concentration of the iron oxide nanoparticles in the solvent is between 0.5 to 1 mg/ml. In other preferred embodiment the concentration of the iron oxide nanoparticles in the solvent is between 0.6 and 0.9 mg/ml. In a more preferred embodiment the concentration of the iron oxide nanoparticles in the solvent is between 0.7 and 0.8 mg/ml.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Example 1

Preparation of the Inoculum

Sludge for inoculation was obtained from mesophilic anaerobic reactors in real wastewater treatment plants. Sludge was obtained from the recirculation of these reactors. This sludge was maintained under staving conditions during two weeks at 37° C. to remove any biodegradable organic matter could interfere in further results.

Example 2

Preparation of Nanoparticles

Different kinds of $Fe_3O_4$ nanoparticles were synthesized in the aqueous phase, using milli-Q grade water. All reagents were purchased from Sigma-Aldrich and used as received.

For $Fe_3O_4$ nanoparticles of 7 nm mean diameter and deoxygenated tetramethylammonium hydroxide (TMAOH) stabilized, based on Massart's method (R. Massart. *Preparation of Aqueous Magnetic Liquids in Alkaline and Acidic Media*. Ieee Transactions on Magnetics 1981, vol. 17(2), pp. 1247-1248)) amounts of 1 mmol iron (II) chloride ($FeCl_2$) and 2 mmol iron (III) chloride ($FeCl_3$) were dissolved in 50 ml of a solution of 1 M (TMAOH). After 30 min of vigorous stirring under a $N_2$ stream, the $Fe_3O_4$ precipitate was washed by soft magnetic decantation and redissolved in 10 mM TMAOH to obtain the final stable colloidal solution of $Fe_3O_4$ nanoparticles.

For $Fe_3O_4$ nanoparticles of 7 nm mean diameter and coated with serum proteins, were mixed fetal bovine serum (FBS) with nanoparticles synthesized with Massart method, at 1:10 FBS:nanoparticles, and left one month for the complete protein adsorption onto nanoparticle surface. All the samples were purified after synthesis to remove $Fe^{2+}$ and $Fe^{3+}$ ions to react as well as chlorine and excess of stabilizers.

For $Fe_3O_4$ nanoparticles of 20 nm mean diameter and deoxygenated tetramethylammonium hydroxide (TMAOH) stabilized, Massart method was also employed but proportions of reactants were changed adapting the ones used in I. Nyiro-Kosa, D. Csakberenyi Nagy and M. Posfai. *Size and shape control of precipitated magnetite nanoparticles*. Eur. J. Mineral. 2009, vol. 21, pp. 293-302. Amounts of 3.4 mmol iron (II) chloride ($FeCl_2$) and 4.2 mmol iron (III) chloride ($FeCl_3$) were dissolved in 50 ml of a solution of 1 M NaOH. After 30 min of vigorous stirring under a $N_2$ stream, the $Fe_3O_4$ precipitate was washed by soft magnetic decantation and redissolved in 10 mM TMAOH. After 30 min of vigorous stirring under a $N_2$ stream, the $Fe_3O_4$ precipitate was washed by soft magnetic decantation and redissolved in 10 mM TMAOH to obtain the final stable colloidal solution of $Fe_3O_4$ nanoparticles.

Table 1 summarizes a description of the nanoparticles previously prepared

TABLE 1

| Nanoparticle Composition | Shape | Diameter (nm) | Surface coating | Nanoparticle/ml | Mg/ml | Solvent (mM) |
|---|---|---|---|---|---|---|
| Iron oxide (Fe3O4) | Irregular | 7 | Inorganic $OH^-$ ions | $10^{15}$ | 0.67 | TMAOH 10 |
| Iron oxide (Fe3O4) | Irregular | 20 | Inorganic $OH^-$ ions | $10^{15}$ | 0.67 | TMAOH 10 |
| Iron oxide (Fe3O4) | Irregular | 7 | Biologic Serum Proteins | $10^{15}$ | 0.67 | Serum proteins 0.1 mM |

Example 3

Determination of Biogas Production

The test methodology to determine anaerobic biogas production was adapted from the German standard DIN-38414 (DIN 38414, 1987. Bestimmung des faulverhaltens (S8). In: Fachgruppe Wasserchemie in der Gesellschaft Deutscher Chemiker und Normausschuss Wasserwesen (NAW) im DIN Deutsches Institut für Normung e.V. (Eds.), Deutsche Einheitsverfahren zur Wasser-, Abwasser-und Schlammuntersuchung, Physikalische, chemische, biologische und bakteriologische Verfahren, VCH Verlagsgesellschaft mbH, Weinheim, Germany).

Anaerobic assays were performed in 600 ml gas tight reactors, equipped with a pressure transducer to monitor biogas production.

Each anaerobic reactor contained 250 ml of inoculum, 250 ml of sample (solvent or nanoparticles suspension, $Fe_3O_4$ nanoparticles of 7 nm mean diameter and deoxygenated tetramethylammonium hydroxide (TMAOH) stabilized), 1.7 g of cellulose and water to 500 ml.

The pH of each reactor was adjusted to 8.

Nitrogen gas was used to purge oxygen previous to incubation to 37° C. during 21 days. Reactors were manually stirred and biogas was purged every workday.

A blank and a reference test were also performed.

The blank test (250 ml of inoculum and water to 500 ml) was performed to subtract biogas production from any biodegradable organic matter contained in the inoculum.

The control test (250 ml of inoculum, 1.7 g of microcrystalline cellulose and water to 500 ml) was performed to compare biogas production with sample test.

Each experiment was carried out in triplicate.

The results are shown as the average value with standard deviation.

As shown in FIG. 1, $Fe_3O_4$ nanoparticles (three replicates (1), (2), (3)) produced and important increase in the biogas production, when compared to control (4).

Figure 2:
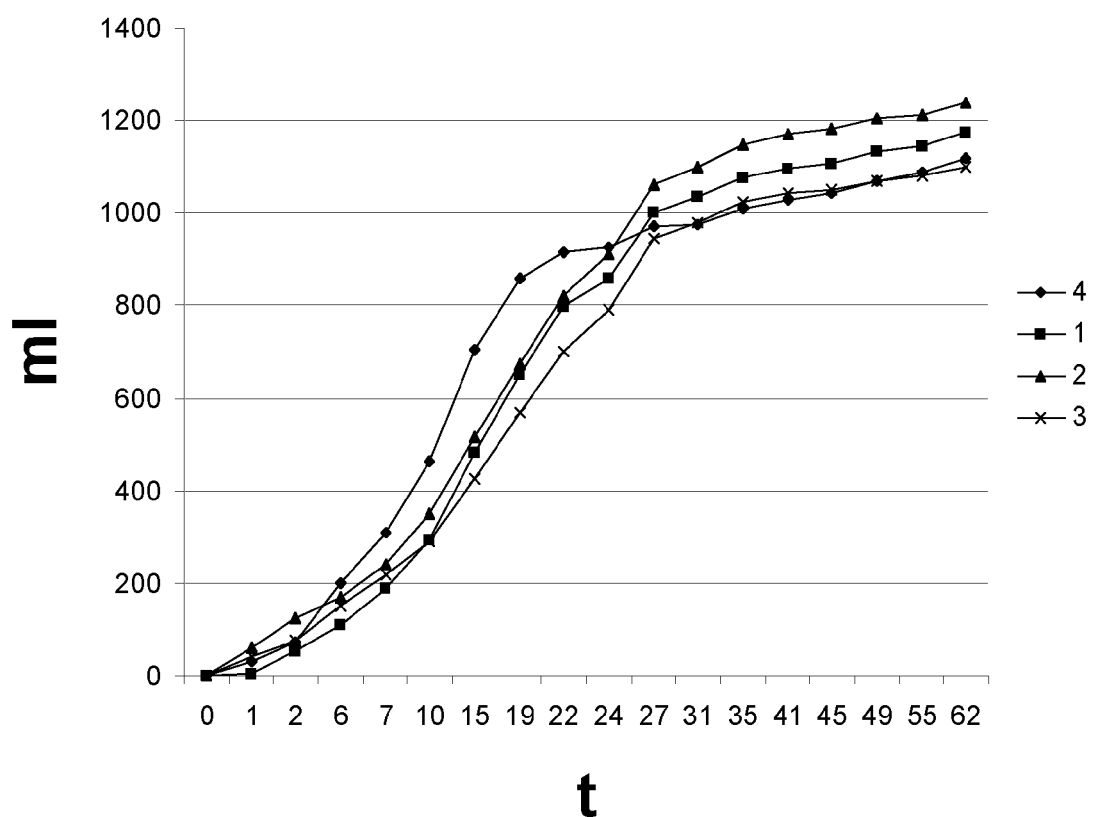
FIG. 2 shows a plot of the production of biogas (ml) versus time, t (days), in the presence of Au nanoparticles (three replicates (5), (6), (7)). The control (8) without nanoparticles is also presented in FIG. 2.

As shown in FIG. 2 gold nanoparticle ((three replicates (4), (5), (6)) and control (8)) produced less ml of biogas than $Fe_3O_4$ nanoparticles.

The $Fe_3O_4$ nanoparticles produced and important increase in the biogas production, when compared to control or when compared to inert nanoparticles such as those of gold. This experiment with $Fe_3O_4$ nanoparticles was repeated under the same conditions several times and the same results were obtained.

Yields of Anaerobic Digestion

Table 2 presents the yields of degradation obtained with the nanoparticles tested based on the content of volatile solid introduced in the reactor in form of cellulose. As can be observed, the biogas produced in the presence of $Fe_3O_4$ was 75% higher than that of the control.

Results are expressed as volume of biogas produced with respect to the initial volatile solid content

| Nanoparticle | Biogas (ml/g) |
|---|---|
| Control | 310 ± 6 |
| $Fe_3O_4$ | 542 ± 7 |
| Ceria oxide | 31 ± 5 |
| Ag | 301 ± 5 |
| Au | 252 ± 6 |
| Titanium oxide | 378 ± 8 |

Figure 3:
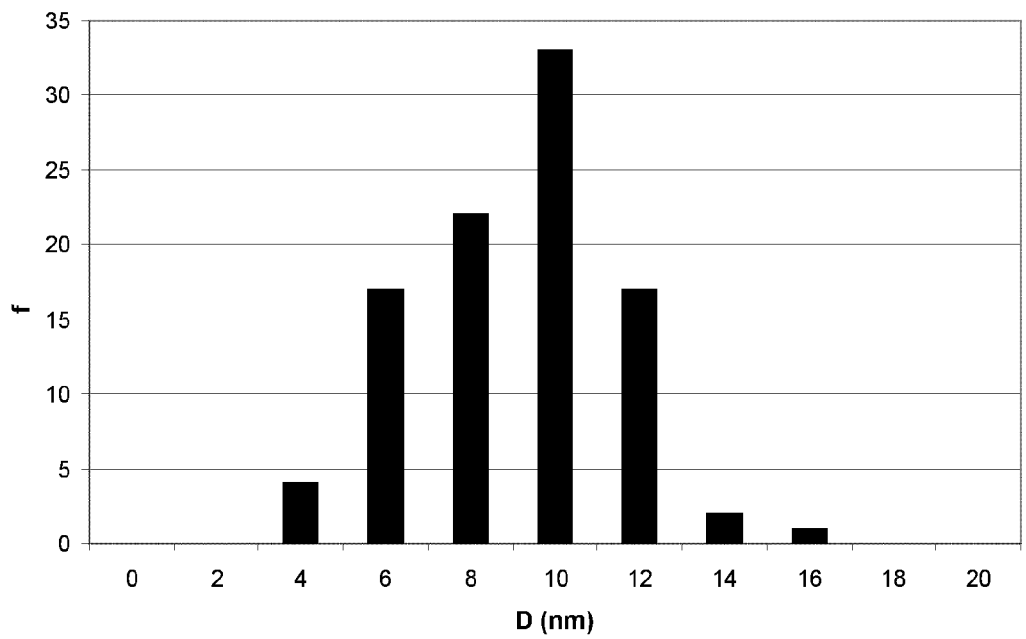
FIG. 3; A: shows a transmission electron microscope (TEM) of the $Fe_3O_4$ nanoparticles as synthesized (frequency, f, versus D (nm)). B: shows a TEM of the $Fe_3O_4$ nanoparticles, after 21 days in the sludge (frequency, f, versus D (nm)).
Figure 3:
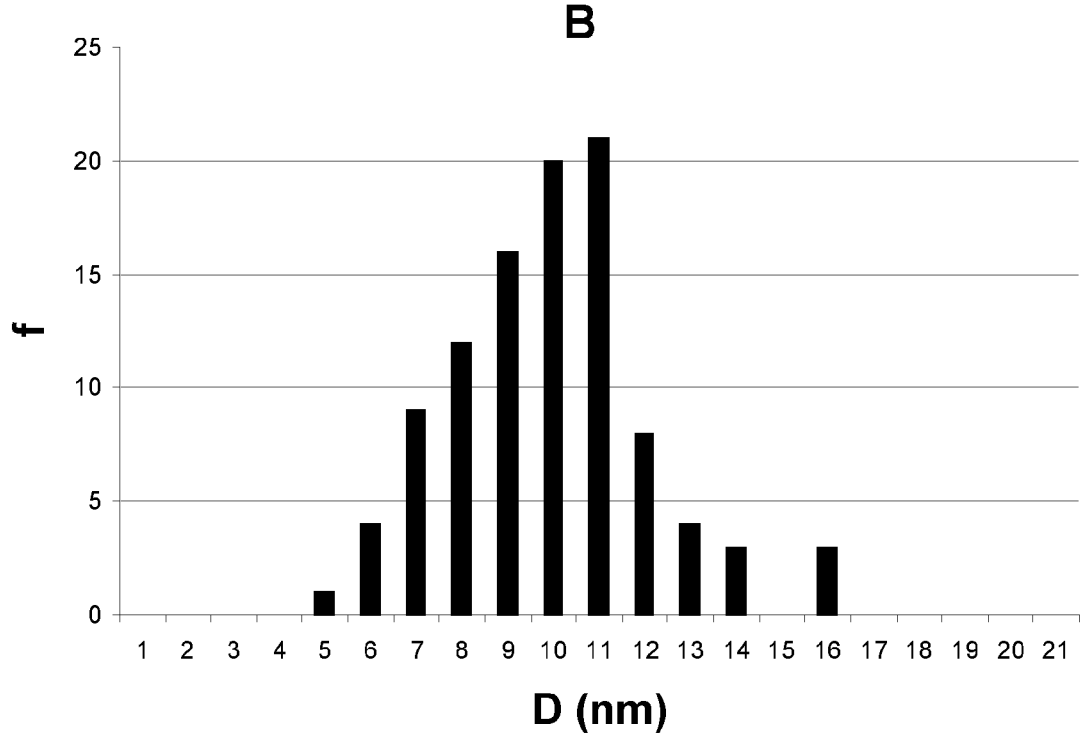

The nanoparticles were observed by TEM, before were introduced in the digester (FIG. 3A) and after 21 days in the sludge (FIG. 3B). The nanoparticles consumed were lost but the nanoparticles that left in the medium are not modified. This means that the presence of ion iron in the media is sustained after 21 days.

Example 4

Determination of the Nanoparticles Behaviour in a Solvent

The $Fe_3O_4$ nanoparticles of 7 nm mean diameter and deoxygenated tetramethylammonium hydroxide (TMAOH) stabilized were dissolved in water and cell culture media.

Figure 4:
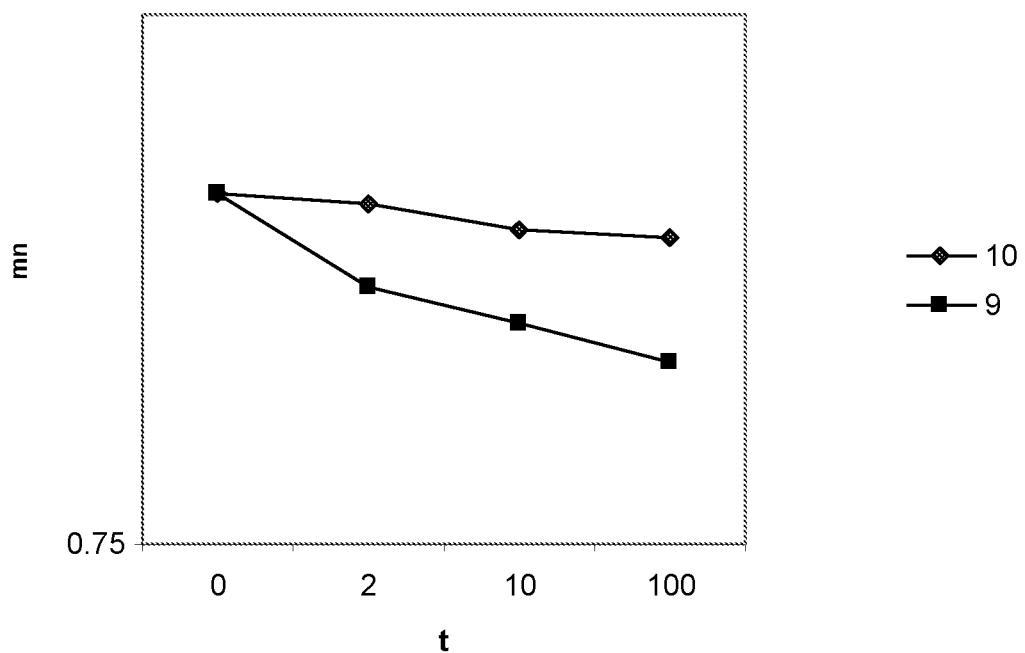
FIG. 4 shows a plot of the mass of nanoparticles, mn (Fe percentage in the nanoparticle with regard to the initial Fe), dissolved in water (9) and cell culture media (10) versus time, t (days).

As it is shown in FIG. 4 the nanoparticles (dissolved in water (9) and cell culture media (10)) yield iron cations. The concentration of iron ions is sustained at a determined concentration for a longer time avoiding the high concentrations corresponding to the nanoparticle inoculation and its rapid decrease.

The FIG. 4 shows the ability of inorganic nanoparticles to control the ion level in solution at different times.

CLAUSES

1. A process for the production of biogas from biodegradable material which comprises the steps of:
(a) adding the biodegradable material to the reactor;
(b) inoculating the microorganisms;
(c) adding a colloidal solution of surface-modified iron oxide nanoparticles to the reactor;
(d) providing anaerobic conditions;
(e) carrying out the anaerobic digestion;
(f) collecting the biogas;
wherein the steps (a), (b) and (c) can be carried out in any order.
2. The process according to claim 1, wherein the iron oxide nanoparticles are Fe3O4 nanoparticles.
3. The process according to any of the claims 1-2, wherein the reaction temperature is between 30° C. and 70° C.
4. The process according to any of the claims 1-3, wherein the microorganisms are mesophilic bacteria.
5. The process according to any of the claims 2-4, wherein the diameter of the iron oxide nanoparticles are between 5 nm and 30 nm.
6. The process according to any of the claims 2-5, wherein the surfaces of the iron oxide nanoparticles are hydroxylated or coated with serum proteins.
7. The process according to any of the claims 2-6, wherein the concentration of the iron oxide nanoparticles are between 0.5 and 1 mg/ml.
8. Use of iron oxide nanoparticles for biogas production in anaerobic conditions.
9. Use according to claim 8, wherein the iron oxide nanoparticles are Fe3O4 nanoparticles.
10. Use according to claim 9, wherein the diameter of the iron oxide nanoparticles are between about 5 nm to about 30 nm.
11. Use according to any of the claims 9-10, wherein the iron oxide nanoparticles are hydroxylated or coating with serum proteins.
12. Use according to any of the claims 9-11, wherein the iron oxide nanoparticles are between about 0.5 to about 1 mg/ml.

The invention claimed is:

1. A process for producing biogas from biodegradable material which comprises the steps of:
(a) adding a biodegradable material to a reactor;
(b) inoculating a microorganism;
(c) adding a colloidal solution of surface-modified iron oxide nanoparticles to the reactor, wherein the diameter of the surface-modified iron oxide nanoparticles is between 3 nm and 30 nm;
(d) providing anaerobic conditions;
(e) carrying out an anaerobic digestion;
(f) collecting the biogas;
wherein the steps (a), (b) and (c) can be carried out in any order.
2. The process according to claim 1, wherein the surface-modified iron oxide nanoparticles are $Fe_3O_4$ nanoparticles.
3. The process according to claim 1, wherein the process is carried out at a temperature between 30° C. and 70° C.
4. The process according to claim 1, wherein the microorganism is a mesophilic bacterium.
5. The process according to claim 2, wherein the diameter of the surface-modified iron oxide nanoparticles is between 3 nm and 20 nm.
6. The process according to claim 2, the surface-modified iron oxide nanoparticles having surfaces, wherein the surfaces of the surface-modified iron oxide nanoparticles are hydroxylated or coated with serum proteins.
7. The process according to claim 2, wherein the surface-modified iron oxide nanoparticles are in a concentration between 0.5 and 1 mg/ml.
8. A method for biogas production in anaerobic conditions and in the presence of iron ions in a biomass medium, the method comprising the steps of:
a) inoculating the biomass medium with a microorganism for anaerobic digestion;
b) adding surface-modified iron oxide nanoparticles capable of supplying iron ions to the biomass medium, wherein the diameters of the surface modified iron oxide nanoparticles are between 3 nm and 30 nm; and
c) collecting biogas.
9. The method according to any of the claim 8, wherein the surface-modified iron oxide nanoparticles are $Fe_3O_4$ nanoparticles.
10. The method according to claim 8, wherein the surface-modified iron oxide nanoparticles are hydroxylated or coated with serum proteins.
11. The method according to claim 8, wherein the surface-modified iron oxide nanoparticles are in a concentration between about 0.5 and about 1 mg/ml.
12. The process according to claim 2, wherein the process is carried out at a temperature between 30° C. and 70° C.
13. The process according to claim 2, wherein the microorganism is a mesophilic bacterium.
14. The process according to claim 3, wherein the diameter of the surface-modified iron oxide nanoparticles is between 3 nm and 20 nm.

15. The process according to claim 3, the surface-modified iron oxide nanoparticles having surfaces, wherein the surfaces of the surface-modified iron oxide nanoparticles are hydroxylated or coated with serum proteins.

16. The process according to claim 3, wherein the surface-modified iron oxide nanoparticles are in a concentration between 0.5 and 1 mg/ml.

17. The process according to claim 3, wherein the microorganism is a mesophilic bacterium.

18. The method according to claim 8, wherein the diameters of the surface modified iron oxide nanoparticles are between 3 nm and 20 nm.

\* \* \* \* \*